United States Patent
Niinomi et al.

(10) Patent No.: US 9,034,017 B2
(45) Date of Patent: May 19, 2015

(54) SPINAL FIXATION ROD MADE OF TITANIUM ALLOY

(71) Applicants: Mitsuo Niinomi, Miyagi-Ken (JP); Masaaki Nakai, Miyagi-Ken (JP); Kengo Narita, Aichi-Ken (JP)

(72) Inventors: Mitsuo Niinomi, Miyagi-Ken (JP); Masaaki Nakai, Miyagi-Ken (JP); Kengo Narita, Aichi-Ken (JP)

(73) Assignees: Showa-Ika Kogyo Co. Ltd., Aichi-ken (JP); National University Corporation Tohoku University, Miyagi-ken (JP)

( * ) Notice: Subject to any disclaimer, the term of this patent is extended or adjusted under 35 U.S.C. 154(b) by 141 days.

(21) Appl. No.: 13/850,913

(22) Filed: Mar. 26, 2013

(65) Prior Publication Data

US 2013/0213535 A1  Aug. 22, 2013

Related U.S. Application Data

(62) Division of application No. 12/965,424, filed on Dec. 10, 2010, now Pat. No. 8,425,567.

(30) Foreign Application Priority Data

Jun. 10, 2010 (JP) ................................. 2010-132886

(51) Int. Cl.
*A61B 17/70* (2006.01)
*C22F 1/18* (2006.01)
*C22C 14/00* (2006.01)
*A61L 31/02* (2006.01)

(52) U.S. Cl.
CPC ........... *C22F 1/183* (2013.01); *Y10T 29/49947* (2015.01); *A61B 17/7002* (2013.01); *C22C 14/00* (2013.01); *A61L 31/022* (2013.01)

(58) Field of Classification Search
CPC ... A61B 17/7002; A61L 31/022; C22F 1/183; C22C 14/00
USPC .................................. 606/254–275, 277–279
See application file for complete search history.

(56) References Cited

U.S. PATENT DOCUMENTS

| 6,607,693 | B1 * | 8/2003 | Saito et al. .................... 420/417 |
| 2004/0241037 | A1 * | 12/2004 | Wu .............................. 420/421 |

* cited by examiner

*Primary Examiner* — Ellen C Hammond
(74) *Attorney, Agent, or Firm* — Osha Liang LLP

(57) ABSTRACT

A spinal fixation titanium alloy rod fixes a plurality of spinal-fixing screws embedded and fixed in vertebrae of a human body. The rod is cylindrically shaped, has a sufficient length for coupling with the spinal-fixing screws, and has a diameter adjusted to 4 to 7 mm. In the titanium alloy constituting the rod, Nb content is 25 to 35 percent by weight, Ta content is such that the Nb content +0.8×Ta content ranges from 36 to 45 percent by weight, Zr content is 3 to 6 percent by weight, and the remainder is Ti and unavoidable impurities, excluding vanadium. The titanium alloy is manufactured by swaging processing at a cross-sectional reduction rate of at least 90%, and aging the swaged titanium alloy by heating at a temperature of 600 to 800K, preferably 700 to 800K, for 43.2 ks to 604.8 ks.

4 Claims, 7 Drawing Sheets

| Working Conditions | Aging Conditions | Tensile Strength | 0.2% Proof Stress | Elongation |
|---|---|---|---|---|
| SW75 | as | 910 | 790 | 16.5 |
|  | 623K | 1330 | 1260 | 11.1 |
|  | 723K | 1080 | 1070 | 16.5 |
| SW90 | as | 850 | 680 | 19.5 |
|  | 623K | 1470 | 1420 | 10.7 |
|  | 723K | 1200 | 1150 | 17.8 |
| SW90 | 43.2 | 1180 | 1050 | 16.2 |
|  | 86.4 | 1200 | 1060 | 15.5 |
|  | 259.2 | 1200 | 1150 | 17.8 |
|  | 604.8 | 1210 | 1160 | 18.1 |
| Ti64 |  | 990 | 860 | 19.3 |

FIG. 8

SPINAL FIXATION ROD MADE OF TITANIUM ALLOY

CROSS-REFERENCE TO RELATED APPLICATIONS

This application is a divisional application and thus claims benefit pursuant to 35 U.S.C. §121, of U.S. patent application Ser. No. 12/965,424 filed Dec. 10, 2010, which claims priority to Japanese Patent Application No. 2010-132886 filed on Jun. 10, 2010, in Japan, the contents of which are incorporated herein by reference.

BACKGROUND OF INVENTION

1. Field of the Invention

The present invention generally relates to a spinal fixation rod made of titanium alloy rod for coupling with and fixing screws used for fixing the spine.

2. Background Art

Typically, a spinal fixation appliance is utilized as a system assembled from various types of parts and is prepared with a size and shape according to the intended use. A typical example suitable as a spinal fixation appliance is a spinal fixation system for fixation of the vertebrae by fixing a plurality of screws embedded in the vertebrae.

The spinal fixation rod is normally shaped as a 4 to 7 mm diameter cylinder having sufficient length for coupling with and fixing the plurality of screws embedded in the vertebrae. During an operation, while the physician elastically deforms the rod to match the curvature of the vertebrae of the spine of the human body, the rod for coupling and fixing the plurality of screws embedded in the vertebrae is coupled to a receiving part of the head part of the screws, and then a rod approximetor is used to fix the rod to the screw heads using set screws.

Providing the rod with biocompatibility is important, because the rod is used by embedding the rod for a long time within the human body. In addition to the rod needs to be capable of being bent by the physician in order to be deformed during the operation to match curvature of the vertebrae of the spine, the rod also preferably does not lose toughness at the bent part. Conversely, a spinal fixation rod embedded in the human body may be subjected to large loads from various angles due to bending and stretching of the vertebrae associated with movement of the human body. Therefore, the rod is required to resist elastic deformation due to a load. However, stress shielding occurs when the spinal fixation appliance is excessively hard in comparison to the bones of the human body. Therefore, the rod preferably has an elastic modulus similar to that of human bone. The rod absolutely must have a fatigue strength of at least a certain value in order to be used long term within the human body. In order for the rod to be capable of use as a spinal fixation rod, the material constituting the rod is required to simultaneously satisfy such mutually contradictory requirements as described above.

Although stainless steel, Co—Cr alloy, pure titanium, and Ti alloy are known as materials for use in a spinal fixation rod, finding a material that satisfies, with good balance, the above-described severe conditions required for a spinal fixation rod is not easy. Among the above-described materials, Ti alloys have recently been frequently used as materials for spinal fixation rods because of their extremely high safety due to resistance to corrosion in the human body and good compatibility with tissues.

Ti alloy spinal fixation rods have been manufactured heretofore as appliances made from Ti-6Al-4V (mass %) alloy, and such spinal fixation rods are used most often due to resistance to elastic deformation due to load (permanent deformation) or the like. However, such Ti alloy spinal fixation rods have been indicated to have problems such as the ready occurrence of stress shielding, because the Ti-6Al-4V alloy has a high elastic modulus in comparison to human bone, vanadium capable of harming the human body is included, and the like.

Under such circumstances, a spinal fixation rod and a spinal fixation system using such a spinal fixation rod are presently needed in order to overcome all the deficiencies of the spinal fixation rods using the Ti-6Al-4V alloy. The spinal fixation rod and spinal fixation system should have characteristics meeting, with good balance, the various requirements for a spinal fixation rod during a spinal fixation operation.

SUMMARY OF INVENTION

An aspect of the present invention is a spinal fixation rod made of titanium alloy for fixing a plurality of spinal fixation screws embedded and fixed in vertebrae of a human body. The rod is cylindrically shaped having a diameter adjusted to 4 to 7 mm and has a sufficient length for coupling with the spinal fixation screws. The titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium. The rod is produced by subjecting a cylindrical rod made of the titanium alloy to a swaging processing of cross-sectional reduction rate of at least 90%, and aging the swaged rod by heating at a temperature of 600 to 800K, preferably 700 to 800K, for 43.2 ks to 604.8 ks.

Another aspect of the present invention is a spinal fixation titanium alloy rod for fixing a plurality of spinal fixation screws embedded and fixed in vertebrae of a human body. The titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium. The titanium alloy rod has properties under JIS of: a) tensile strength is greater than or equal to 1,150 MPa, b) fatigue strength is greater than 900 MPa, c) elastic modulus is less than 110 GPa, d) 0.2% proof stress is greater than 1,000 MPa, and e) percentage elongation after fracture is greater than or equal to 15%.

Another aspect of the present invention is a spinal fixation rod made of titanium alloy for fixing a plurality of spinal-fixing screws embedded and fixed in vertebrae of a human body. The rod is produced by subjecting a cylindrical rod made of titanium alloy to a swaging processing of a cross-sectional reduction rate greater than or equal to 90% wherein the titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium, aging the swaged titanium alloy by heating at a temperature of 700 to 800K for 43.2 ks to 604.8 ks; and machining the aged titanium alloy into a cylindrical shape having a diameter of 4 to 7 mm.

Another aspect of the present invention is method for producing a spinal fixation rod made of titanium alloy for fixing a plurality of spinal fixation screws embedded and fixed in vertebrae of a human body. The method comprises: subjecting a cylindrical rod made of the titanium alloy to a swaging processing of a cross-sectional reduction rate greater than or equal to 90% wherein the titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium; aging the swaged titanium alloy rod by heating at a temperature of 700 to 800K for 43.2 ks to 604.8 ks; and precision machining the aged titanium alloy rod into a cylindrical shape having a diameter of 4 to 7 mm.

Another aspect of the present invention is a spinal fixation system. The system comprises: a plurality of screws made of titanium alloy; a spinal fixation rod manufactured by steps comprising: subjecting a cylindrical rod made of titanium alloy to a swaging processing of a cross-sectional reduction rate greater than or equal to 90% wherein the titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium; and aging the swaged titanium alloy by heating at a temperature of 600K to 800K, preferably 700K to 800K for 43.2 ks to 604.8 ks; and a plurality of set screws for fixing the plurality of screws with the rod, the set screws being made of stainless Ti-6Al-4V alloy.

Another aspect of the present invention is a method for connecting a plurality of screws that are screwed into a plurality of vertebrae. The method comprises: screwing a plurality of the spinal fixation screws into the plurality of vertebrae, the screw having a rod receiver at a top part; placing a spinal fixation rod within the receiver, the rod being produced by: subjecting a cylindrical rod made of the titanium allow to a swaging processing of cross-sectional reduction rate greater than or equal to 90% wherein the titanium alloy comprises Nb content of 25 to 35 percent by weight, Ta content of such that the Nb content +0.8×Ta content ranges from 36 to 45 percent by weight, Zr content of 3 to 6 percent by weight, and the remainder is Ti and unavoidable impurities, excluding vanadium; and aging the swaged titanium alloy by heating at a temperature of 600 to 800K for 43.2 ks to 604.8 ks; and fixing the rod with the screw using a rod approximetor.

Other aspects and advantages of the invention will be apparent from the following description and the appended claims.

BRIEF DESCRIPTION OF DRAWINGS

FIG. 8 shows results of measurement of tensile strength, 0.2% proof stress, and elongation for the TNTZ alloy according to one or more embodiments of the present invention.

DETAILED DESCRIPTION

Embodiments of the present invention are explained below, referring to the attached figures. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Figure 1:
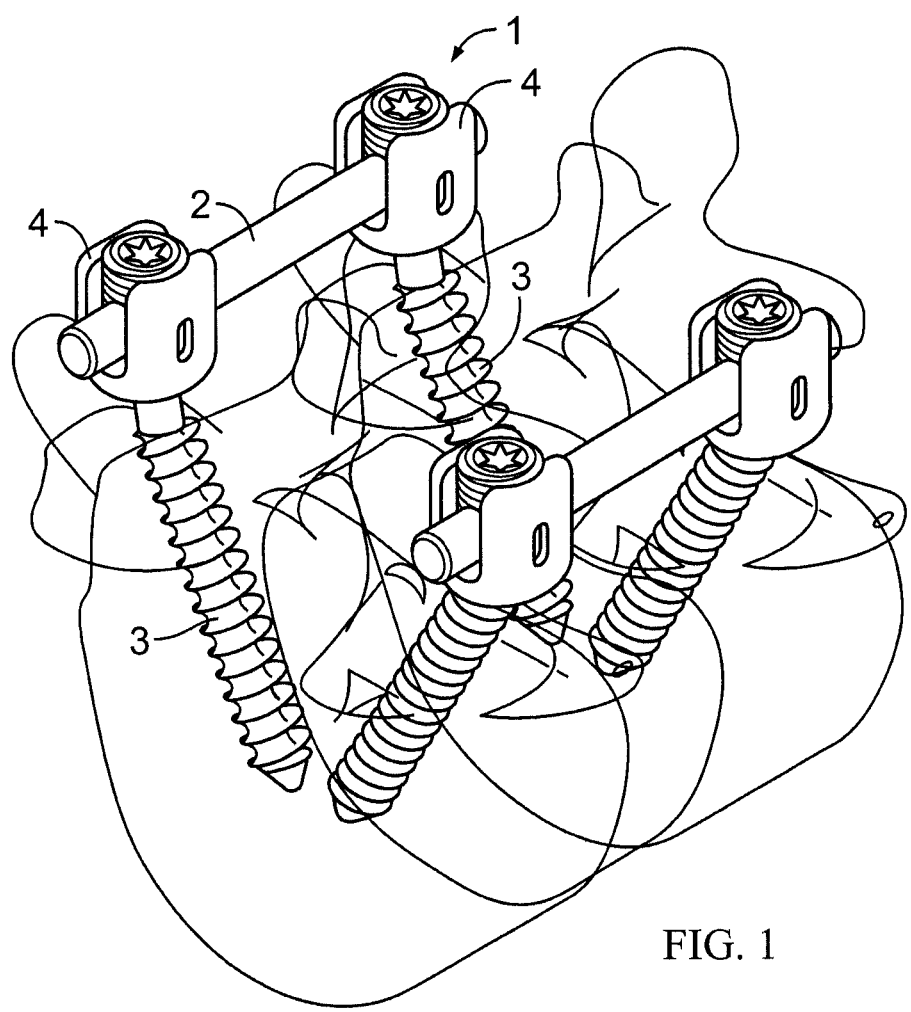
FIG. 1 shows a tilted perspective drawing of a spinal fixation appliance using a spine fixation titanium alloy rod according to one or more embodiments of the present invention.

FIG. 1 is a tilted perspective view of the spinal fixation appliance 1 using a spinal fixation titanium alloy rod 2 of the present invention. As shown in FIG. 1, the spinal fixation appliance 1 has a spinal fixation rod 2 and a screw 3. By fixing both tip sides of the spinal fixation rod 2 through the set screws 6 to the head parts 4 of the screws 3 embedded in the vertebrae 5, the vertebrae 5 are fixed together. The spinal fixation rod 2 in this manner is used as part of the spinal fixation appliance 1 for fixing the spine.

In the titanium alloy used in the spinal fixation titanium alloy rod in one or more embodiments of the present invention, the Nb content is 25 to 35 percent by weight, Ta content is such that the Nb content +0.8×Ta content ranges from 36 to 45 percent by weight, Zr content is 3 to 6 percent by weight, and the remainder is Ti and unavoidable impurities, excluding vanadium (hereinafter, this Ti alloy composition will be abbreviated as the "TNTZ alloy").

The above-described round rod formed from TNTZ alloy can be manufactured, for example, by levitation melting of a powder of the above-described various metals at the above-described weight percent concentrations, thereafter casting to form an ingot, and, then, hot forging to produce a round rod of about 24 mm diameter. This round rod-shaped casting can be subjected to solution heat treatment. Such solution heat treatment, for example, can be performed by heating the round rod for 0.6 ks to 3.6 ks at a temperature of 973 to 1,073K and then water cooling the heat treated round rod. A method for the manufacture of TNTZ alloy is disclosed in Japanese Laid-Open Unexamined Patent Application 2002-18016, which is incorporated by reference as part of the present application.

The above-described 24 mm diameter Ti alloy round rod is swaged at a cross-sectional reduction rate of at least 90% to produce a round rod of 7 mm diameter. In this context, swaging refers to beating while rotating the round rod to cold work and reduce diameter of the round rod. When swaging of an α+β phase Ti alloy (e.g. Ti-6Al-4V) is performed so that the cross-sectional reduction rate is greater than or equal to 90%, cracks form in the workpiece or the workpiece breaks. However, TNTZ alloy has β phase as a mother phase and, thus, there is no concern that cracking or breaking will occur even when the workpiece is subjected to extreme swaging (i.e. greater than or equal to 90%).

Immediately after the above-described swaging, the TNTZ alloy is subjected to aging treatment. During the aging treatment, the heating temperature is set in the range of 600K to 800K, preferably 700K to 800K, and the TNTZ alloy is heated for 43.2 ks to 604.8 ks.

Although it is not necessarily clear what chemical changes occur in the TNTZ alloy due to the above-described swaging and subsequent aging treatment, it has been found by the inventors of the present invention that a large amount of dislocations are introduced into the grains of the β phase rather than there being a change in the crystal structure (β phase) of the TNTZ alloy. It is believed that a large amount of the fine α phase precipitates within the β phase grains due to the heating during the post-swaging aging treatment.

The titanium alloy rod manufactured in this manner has the mechanical properties of an elastic modulus (Young's modulus) ranging between 60 GPa and 110 GPa, an tensile strength greater than 1,150 MPa, a fatigue strength greater than 900 MPa, a 0.2% proof stress greater than 1,000 MPa, and an elongation greater than or equal to 15%. Tensile strength, 0.2% proof stress (proof stress calculated by off set method) and percentage elongation after fracture are measured in accordance with JIS Z 2241 (method of tensile test for metallic materials) of 1993 version. Fatigue strength is measured in accordance with the method described in JIS Z 2273 (General rules for fatigue testing of metals) of 1974. Young's modulus is measured in accordance with the method described in JIS Z 2280 (Test method for Young's modulus of metallic materials at elevated temperature) of 1993. Disclosure of these JIS is incorporated by reference as part of the present application.

The Young's modulus of the TNTZ alloy manufactured in the above-described manner is low in comparison to Ti-6Al-4V alloy. Thus, when TNTZ alloy spinal fixation rod is implanted in the human body, there is less concern that stress shielding may occur in comparison to the rod manufactured from Ti-6Al-4V alloy.

Fatigue strength of the TNTZ alloy rod manufactured in the above-described manner is greater than 900 MPa. This value is excellent in comparison to the fatigue strength of the rod manufactured from the conventional Ti-6Al-4V alloy, fatigue strength of which is about 725 MPa. According to findings of the inventors of the present invention, due to swaging and the post-swaging aging treatment, the α phase precipitates within the grains of the β phase (mother phase) of the TNTZ alloy, and this is believed to stop the promotion of fatigue cracks by the α phase.

Proof stress (0.2% proof stress) of the TNTZ alloy rod manufactured in the above-described manner, which is measured as proof stress calculated by offset method in accordance with JIS Z 2241 of 1993, ranges from 1,000 MPa to 1,300 MPa. When the proof stress ranges from 1,000 MPa to 1,300 MPa, the physician during the operation is able to plastically deform the rod to match curvature of the spine of the patient.

Percentage elongation after fracture of the rod manufactured from TNTZ alloy becomes greater than or equal to 15% due to the above-described post-swaging aging treatment for 3.2 ks to 604.8 ks at a temperature of at least 700K. When the post-swaging aging treatment is performed at a temperature somewhat lower than 700K (e.g. 673K), although the obtained TNTZ alloy rod has excellent tensile strength and 0.2% proof stress, elongation is low, i.e. about 11%. When the post-swaging aging treatment is instead performed at a temperature of at least 700K (e.g. 723K), excellent physical properties are obtained, including percentage elongation after fracture of at least 15%. When swaging and aging treatment are performed under such high temperature, TNTZ alloy rod tensile strength and proof stress (0.2% proof stress) are not lost.

When the spinal fixation rod is plastically deformed by bending by the physician during the operation, toughness of the bend part may be lost due to such bending deformation, and such loss of toughness may be undesirable for a rod implanted in the human body. When percentage elongation after fracture of the TNTZ alloy used in the spinal fixation rod is greater than or equal to 15%, bending of the rod by the physician during the operation does not cause toughness of the bent part to be lost after plastic deformation. Thus, if the spinal fixation rod satisfies other physical properties required for a spinal fixation rod (i.e. tensile strength, elastic modulus, proof stress, fatigue strength, and the like), and if the spinal fixation rod also has an elongation greater than or equal to 15%, then the spinal fixation rod can be said to have a quite excellent balance of physical properties.

The inventors of the present invention found that, by swaging TNTZ alloy at a cross-sectional reduction rate of 90% and, then, by performing aging treatment at a temperature of at least 700K, it was possible to improve fatigue strength without a loss of the basic physical properties required for the spinal fixation rod, and in comparison to aging treatment at a lower temperature, it was simultaneously possible to dramatically improve elongation by performing the aging treatment at the temperature of at least 700K. The inventors of the present invention also found that, even after performance of such extreme working, the other basic physical properties required for a spinal fixation rod were sufficiently maintained, i.e., tensile strength and proof strength (0.2% proof strength). Based on these discoveries, the inventors of the present invention conceived of the use of the manufactured TNTZ alloy worked in this manner as a spinal fixation rod and conceived of a spinal fixation system using this type of TNTZ alloy.

Fatigue strength, tensile strength, proof strength, Young's modulus, and elongation of the TNTZ alloy of the present invention were tested in the below described manner.

EXPERIMENT 1

EXAMPLES 1 AND 2, COMPARATIVE EXAMPLE 1

Table 1 shows the composition (percent by weight) of the hot forged round rod prepared as the test sample. This test sample had not been subjected to solution heat treatment. Thereafter, this test sample was swaged at room temperature so that the cross-sectional reduction rate became 91%.

TABLE 1

| Test sample (percent by weight) | Nb | Ta | Zr | O | N | Nb + 0.8Ta | Ti |
|---|---|---|---|---|---|---|---|
| SW-rod | 29.9 | 13.3 | 4.73 | 0.110 | 0.008 | 40.54 | Remainder |

Thereafter, the above-described test sample was subjected to aging treatment by maintenance in a vacuum for 72 hours (259.2 ks) at 400° C. (673K) during example 1 or at 450° C. (723K) during example 2. The sample was thereafter cooled using water. The rod obtained during example 1 (673K) is referred to below as the SW-rod$_{673K}$, and the rod obtained during example 2 (723K) is referred to below as the SW-rod$_{723K}$. The sample from comparative example 1, which had not undergone post-swaging aging treatment, is referred to as the SW-rod$_{as}$.

COMPARATIVE EXAMPLES 2, 3, 4, 5, AND 6

Table 2 shows the composition of the hot forged round rod prepared during comparative example 2. This test sample was solution heat treated by being held for 1 hour (3.6 ks) in a vacuum at 790° C. (1,063K), followed by water cooling.

During comparative example 3, after solution heat treatment in the same manner as during comparative example 2, aging treatment was performed by maintenance of the sample for 72 hours (259.2 ks) in a vacuum at 400° C. (673K), followed by water cooling. During comparative example 4, after solution heat treatment in the same manner as during comparative example 2, aging treatment was performed by maintenance of the sample for 72 hours (259.2 ks) in a vacuum at 450° C. (723K), followed by water cooling.

During comparative example 5, after solution heat treatment in the same manner as during comparative example 2, the test sample was subjected to aging treatment by maintenance for 72 hours (259.2 ks) in a vacuum at 400° C. During comparative example 6, after solution heat treatment in the same manner as during comparative example 2, the test sample was subjected to aging treatment by maintenance for 72 hours (259.2 ks) in a vacuum at 450° C.

The titanium alloy rods obtained during comparative examples 2, 3, and 4 are referred to below as ST-rod$_{as}$, ST-rod$_{673K}$, and ST-rod$_{723K}$, respectively. Comparative examples 5 and 6 are referred to below as CR-rod$_{673K}$ and CR-rod$_{723K}$, respectively.

TABLE 2

| Test sample (percent by weight) | Nb | Ta | Zr | O | N | Nb + 0.8Ta | Ti |
|---|---|---|---|---|---|---|---|
| ST-rod | 30.5 | 13.0 | 4.81 | 0.078 | 0.09 | 40.9 | Remainder |

COMPARATIVE EXAMPLE 7

A Ti-6Al-4V ELI alloy rod (referred to as the Ti64-rod) actually used as a spinal fixation rod was prepared.

EVALUATION OF EXAMPLES AND COMPARATIVE EXAMPLES

The detailed composition of each sample from each of the rods obtained during examples 1 and 2 was observed by optical microscopy and field emission scanning electron microscopy (FE-SEM). The constituent phases of each sample were identified using X-ray diffraction (XRD). During evaluation of mechanical characteristics, Young's modulus was measured by the free resonance method, and tensile testing and fatigue testing were both carried out at room temperature in air. Tensile testing was performed using an Instron (R) type tensile tester at a cross head speed of 8.33× 10$^{-6}$ m/sec. Fatigue testing was performed using a hydraulic type fatigue tester, 0.1 stress ratio, and 10 Hz frequency.

Figure 2:
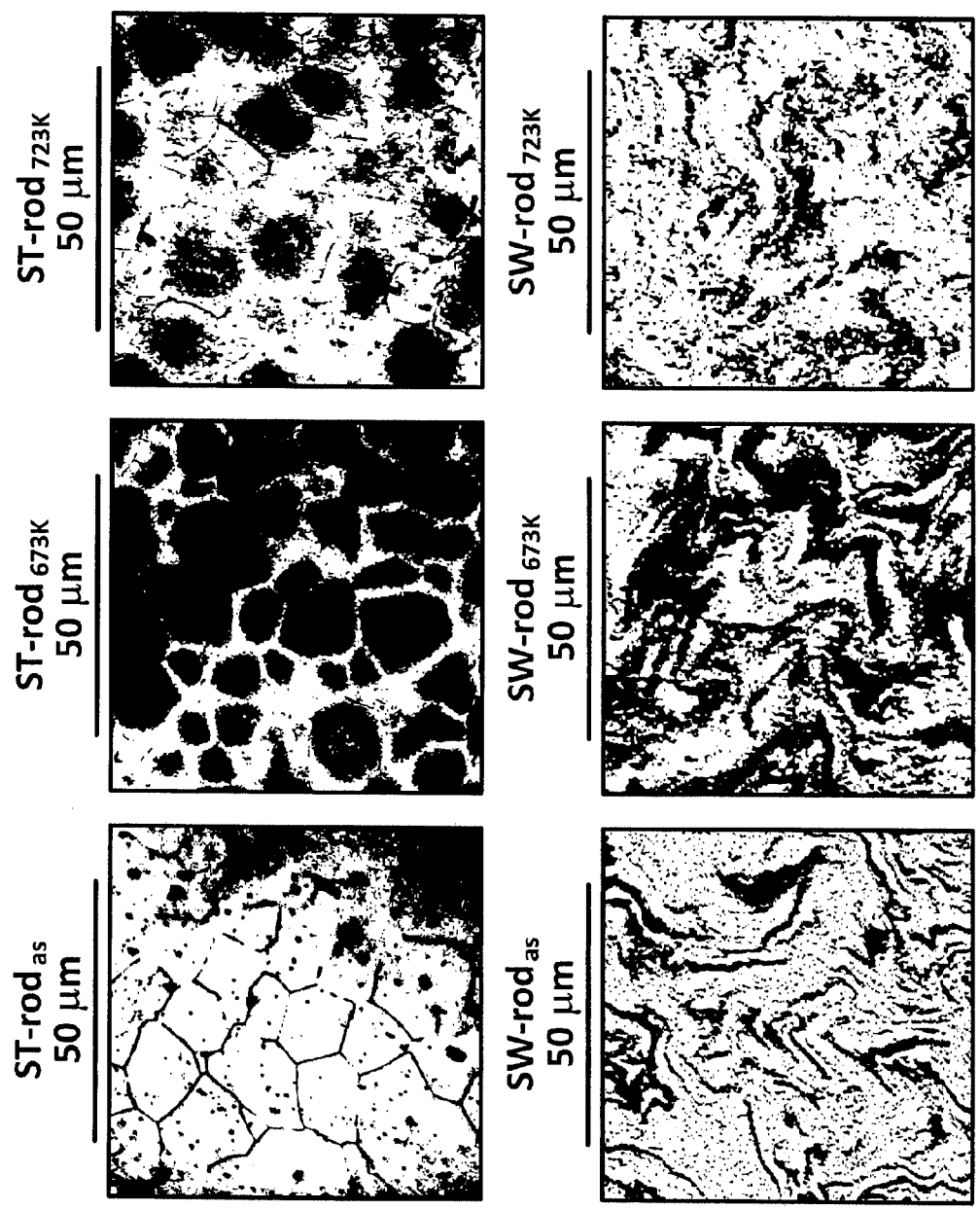
FIG. 2 shows a figure showing results of optical microscopy structure observations for the rods of examples 1 and 2 according to one or more embodiments of the present invention, and comparative examples 2, 3, and 4.

Results of optical microscopic observation of structure are shown in FIG. 2. Equiaxed grains were not found for SW-rod$_{as}$, SW-rod$_{673K}$, and SW-rod$_{723K}$ (comparative example 1 and examples 1 and 2, respectively), which had been subjected to swaging at room temperature to reach a 91% cross-sectional reduction rate, and each of these was found to have a marble-like structure.

Figure 3:
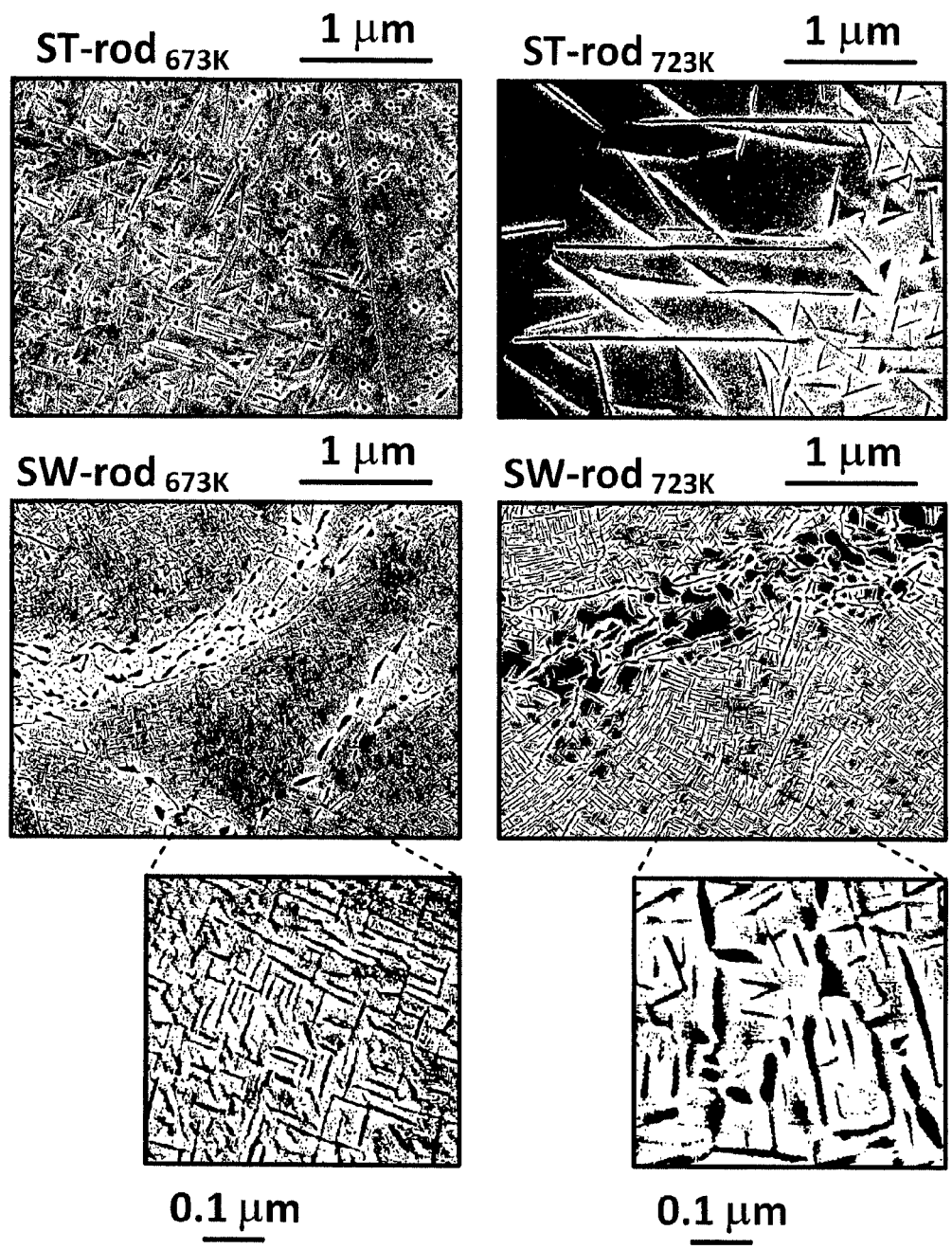
FIG. 3 shows is a figure showing results of FE-SEM structure observations for the rods of examples 1 and 2 according to one or more embodiments of the present invention, and comparative examples 3 and 4.

The fine structure observation results using FE-SEM are shown in FIG. 3. In SW-rod$_{673K}$ (example 1), a sub-granular structure was found to have formed along the marble-like structure shape. An extremely fine needle-like precipitated phase (α phase) was found therein. In SW-rod$_{723K}$ (example 2), a sub-granular structure was also found to have formed along the marble-like structure shape. Although an extremely fine needle-like precipitated phase (α phase) was also found, the size of this precipitated phase was large in comparison to that of SW-rod$_{673K}$ (example 1).

Figure 4:
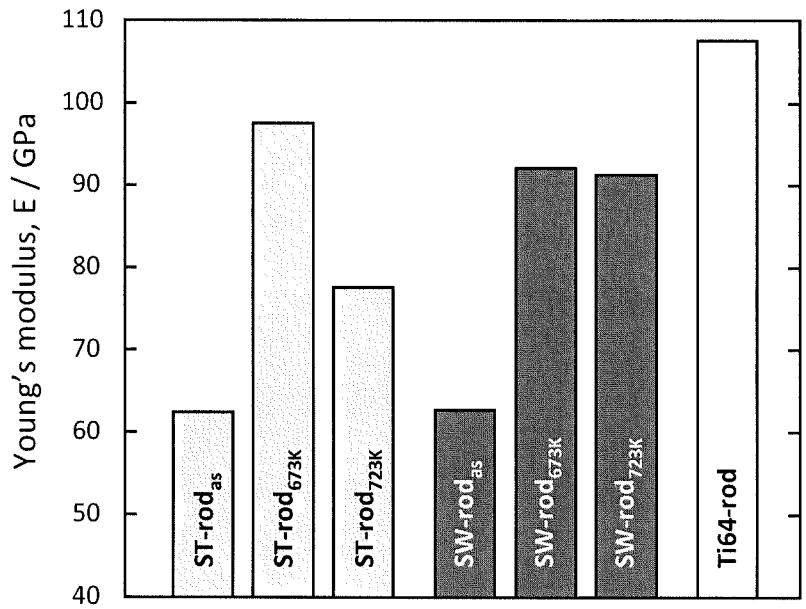
FIG. 4 shows results of measurement of the Young's modulus by the free resonance method for the rods of examples 1 and 2 according to one or more embodiments of the present invention, and comparative examples 1, 2, 3, 4, and 7.

FIG. 4 shows results of measurement of Young's modulus by the free resonance method. Although only the α phase was found to have precipitated in both SW-rod$_{673K}$ (example 1) and SW-rod$_{723K}$ (example 2), a high density of dislocations were introduced by swaging, and this is thought to have promoted the precipitation of the α phase during these examples. In both SW-rod$_{673K}$ (example 1) and SW-rod$_{723K}$ (example 2), Young's modulus was about 90 GPa, and a comparatively large increase in Young's modulus was found. However, in comparison to the Young's modulus (about 110 GPa) of the Ti-6Al-4V rod (comparative example 7), both of these TNTZ rods maintained a lower value Young's modulus. The ability to control Young's modulus at a lower value than that of Ti-6Al-4V despite the TNTZ rod having undergone extreme working (i.e. swaging at a cross-sectional reduction rate of at least 90% and aging treatment at a temperature of at least 700K) is important in that the TNTZ rod can then be used as a spinal FIXATION rod.

Figure 5:
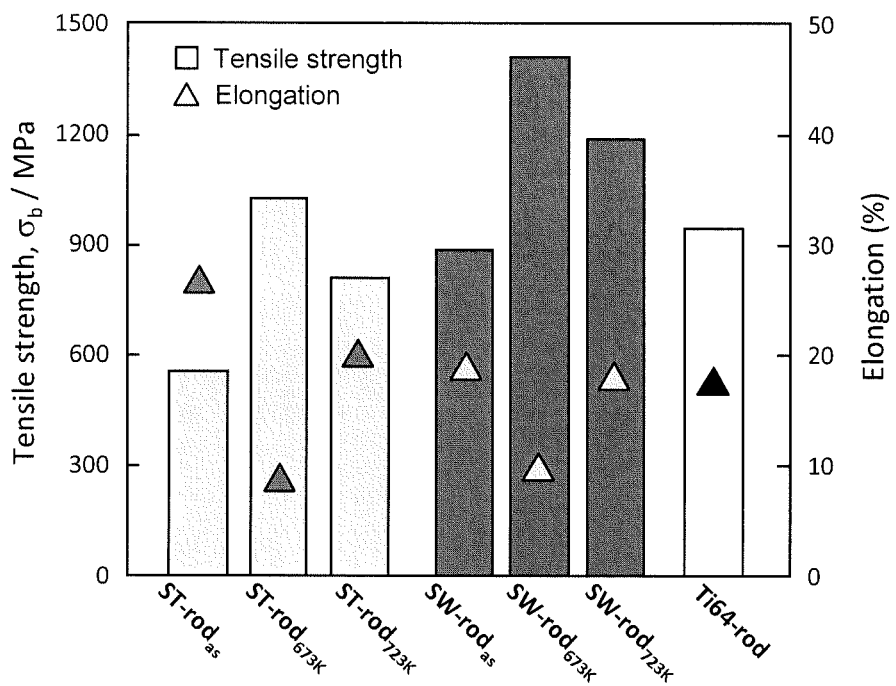
FIG. 5 shows results of measurement of tensile testing for the rods of examples 1 and 2 according to one or more embodiments of the present invention, and comparative examples 1, 2, 3, 4, and 7.

Results of tensile testing are shown in FIG. 5.

In comparison to ST-rod$_{673K}$ (comparative example 3), SW-rod$_{673K}$ (example 1) had a large improvement in tensile strength despite having similar elongation. In comparison to ST-rod$_{723K}$ (comparative example 4), SW-rod$_{723K}$ (example 2) had a large improvement in tensile strength despite having similar elongation. Tensile strength for the SW-rod$_{673K}$ (comparative example 3) and SW-rod$_{723K}$ (comparative example 4) favorably compared with that of the Ti64-rod (comparative example 7). Based on these tensile test results, SW-rod$_{673K}$ (experiment 1) and SW-rod$_{723K}$ (experiment 2) can be said to have an excellent balance of strength and ductility.

Figure 6:
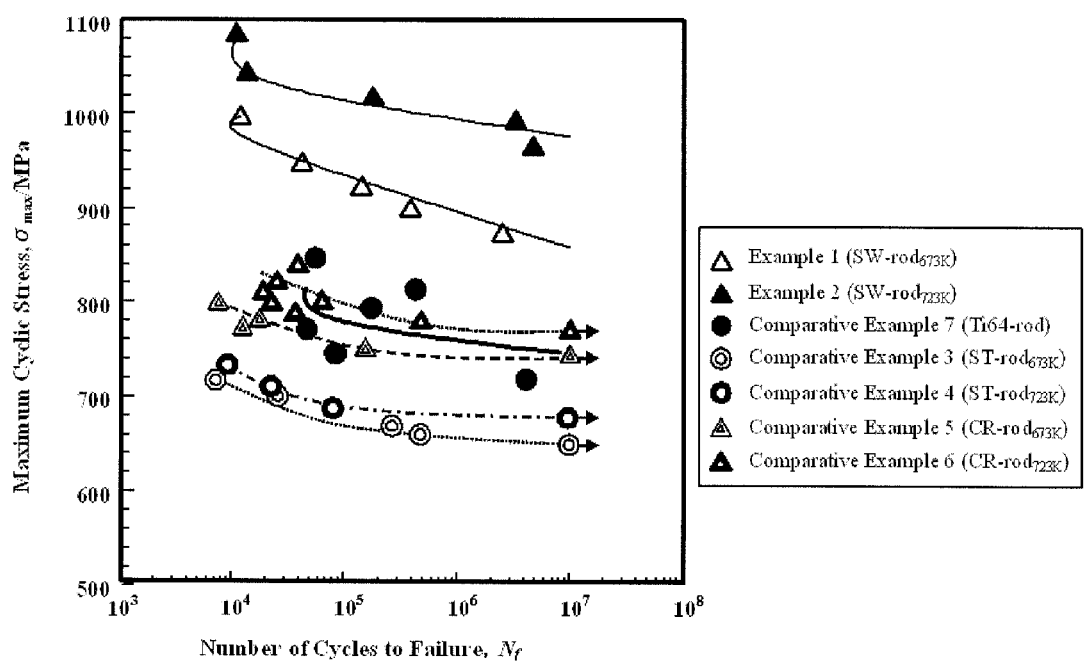
FIG. 6 shows results of measurement of fatigue testing for the rods of examples 1 and 2 according to one or more embodiments of the present invention, and comparative examples 1, 2, 3, 4, and 7.

Fatigue testing results are shown in FIG. 6. Fatigue strength is the value of the maximum cyclic stress at 10$^7$ cycles of repeated stress. Fatigue strength of the Ti64-rod (comparative example 7) is indicated by the bold-continuous-line curve and had a value of about 750 MPa. Fatigue strengths of SW-rod$_{673K}$ (example 1) and SW-rod$_{723K}$ (example 2) were indicated by non-bold continuous-line curves and had values of about 850 MPa and about 950 MPa, respectively. Therefore, fatigue strengths of the SW-rod$_{673K}$ (example 1) and SW-rod$_{723K}$ (example 2) were both found to be higher than that of the Ti64-rod (comparative example 7). Fatigue strength values of comparative examples 3-6 were at or below those of comparative example 7.

Table 3 shows results of the evaluations of examples 1 and 2 and comparative examples 1-6. Tensile strength, elastic modulus, and fatigue strength of examples 1 and 2 and comparative examples 1-6 are indicated in comparison to comparative example 7.

TABLE 3

| | Composition | Working method | Tensile strength | Elastic modulus | Fatigue strength |
|---|---|---|---|---|---|
| example 1 | Ti—29Nb—13Ta—4.6Zr | swaging + aging | high | low | High |
| example 2 | Ti—29Nb—13Ta—4.6Zr | swaging + aging | high | low | High |
| comparative example 1 | Ti—29Nb—13Ta—4.6Zr | swaging | approximately same | low | |
| comparative example 2 | Ti—29Nb—13Ta—4.6Zr | solution heat treatment | low | low | |
| comparative example 3 | Ti—29Nb—13Ta—4.6Zr | solution heat treatment + aging | approximately same | low | Low |
| comparative example 4 | Ti—29Nb—13Ta—4.6Zr | solution heat treatment + aging | approximately same | low | Low |
| comparative example 5 | Ti—29Nb—13Ta—4.6Zr | solution heat treatment + rolling + aging | high | low | Low |
| comparative example 6 | Ti—29Nb—13Ta—4.6Zr | solution heat treatment + rolling + aging | high | low | Low |
| comparative example 7 | Ti—6Al—4V | | standard | standard | standard |

*plate-shaped test piece

According to the above listed results, examples 1 and 2 had excellent fatigue strength, and elastic modulus is understood to have been lower than that of comparative example 7. Moreover, because fatigue strength of examples 1 and 2 was higher than that of comparative examples 3 and 4, it is understood that the combination of swaging and aging treatment was good for processing titanium alloy. Because fatigue strength of examples 1 and 2 was higher than that of comparative examples 5 and 6, it is understood that swaging was better than rolling as a cold working method for titanium alloy. Although solution heat treatment was not performed during examples 1 and 2, even if solution heat treatment had been performed prior to swaging, in a manner similar to that of the above-described examples, it is anticipated that a TNTZ rod could be obtained with a higher fatigue strength than that of the Ti64-rod.

EXPERIMENT 2

Figure 7:
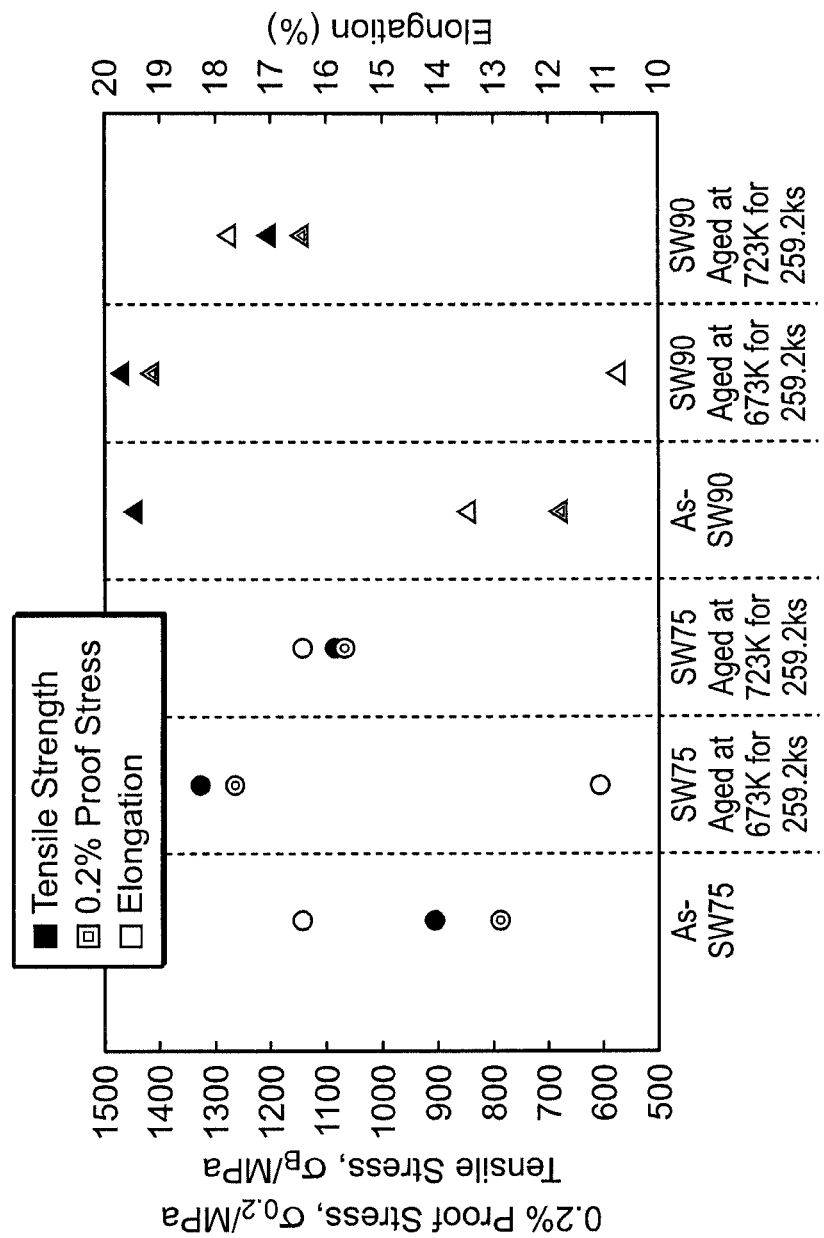
FIG. 7 shows results of measurement of tensile strength, 0.2% proof stress, and elongation for the TNTZ alloy according to one or more embodiments of the present invention.

TNTZ alloy was manufactured with a Nb content of 29 percent by weight, Ta content of 13 percent by weight, and Zr content of 4.6 percent by weight, with the remainder as Ti. This TNTZ alloy was swaged at 75% or 90% cross-sectional reduction rates. The TNTZ alloy swaged at the 75% cross-sectional reduction rate was designated as As-SW75, and the TNTZ alloy swaged at the 90% cross-sectional reduction rate was designated as As-SW90. Thereafter, these swaged TNTZ alloys were subjected to aging treatment for 259.2 ks at a temperature of 673K and 723K. The 75% cross-sectional reduction rate-swaged TNTZ alloy subjected to aging treatment at 673K for 259.2 ks was designated as "SW75 aged at 673K for 259.2 ks." The 90% cross-sectional reduction rate-swaged TNTZ alloy subjected to aging treatment at 723K for 259.2 ks was designated as "SW90 aged at 723K for 259.2 ks." Results of measurement of tensile strength, 0.2% proof stress, and elongation for the TNTZ alloys obtained in this manner are shown in FIG. 7 through FIG. 8. FIG. 7 shows tensile properties of TNTZ sample subjected to aging treatment after cold swaging as functions of reduction ratio and aging temperature. In FIGS. 7 and 8, "Elongation" means percentage elongation after fracture measured in accordance with JIS Z 2241 (Method of tensile test for metallic materials) of "0.2% Proof stress" means proof stress calculated by offset method as described in the JIS Z 2241.

As may be understood from FIG. 7 through FIG. 8, the samples of TNTZ alloy that had been swaged at 75% and 90% cross-sectional reduction rates but had not been subjected to aging treatment (i.e. As-SW75 and As-SW90, respectively), had tensile strength values that were both no greater than 900 MPa, and 0.2% proof stress values were both no greater than 800 MPa. However, elongation values for As-SW75 and As-SW90 were both at least 15%. Looking at elongation values alone, As-SW75 and As-SW90 both displayed values of at least 15%, and there appeared to be no deterioration of toughness at the bent part of the rod. However, fatigue strength of the TNTZ alloy was low if the alloy had not been subjected to post-swaging aging treatment and, thus, As-SW75 and As-SW90 would be difficult to use as materials for a spinal fixation rod.

When the TNTZ alloy rods swaged at the 75% and 90% cross-sectional reduction rate were subjected to aging treatment by heating to 673K or 723K for 259.2 ks, elongation was low when the heating temperature was 673K. However, when these rods were heat treated at a heating temperature 50K higher (i.e. at 723K), it was determined that elongation was much higher for both the 75% and 90% cross-sectional reduction rate TNTZ alloy rods.

From the standpoints of tensile strength, 0.2% proof stress, and elongation, the best balance of physical properties is displayed in FIG. 7-FIG. 8 for the TNTZ alloy rods that had been subjected to swaging at 90% cross-sectional reduction rate followed by aging treatment by heating for 259.2 ks at 723K.

When swaging is performed at a cross-sectional reduction rate of at least 90% and then aging treatment is performed by heating for 259.2 ks at 723K, it is understood from the results of experiment 1 and experiment 2 that excellent physical properties are provided for a spinal fixation rod. It is understood that such physical properties are equivalent or better than those of the conventionally used Ti-6Al-4V with respect to each of the properties of fatigue strength, tensile strength, 0.2% proof stress, and elongation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for producing a rod made of titanium alloy, the method comprising:
   forming a cylindrical round rod of the titanium alloy, wherein the titanium alloy comprises:
   Nb content of 25 to 35 percent by weight,
   Ta content of such that the Nb content +0.8×Ta content ranges from 36 to 45 percent by weight,
   Zr content of 3 to 6 percent by weight, and
   the remainder is Ti and unavoidable impurities, excluding vanadium;
   subjecting the cylindrical round rod made of the titanium alloy to a swaging processing of a cross-sectional reduction rate greater than or equal to 90%; and
   aging the swaged titanium alloy rod by heating at a temperature of 700 to 800K for 43.2 ks to 604.8 ks.

2. The method according to claim 1, further comprising machining the aged titanium alloy rod into a cylindrical shape having a diameter of 4 to 7 mm.

3. The method according to claim 2, wherein the machining of the aged titanium alloy rod is performed such that the rod has a sufficient length for coupling with spinal fixation screws embedded and fixed in vertebrae of a human body.

4. The method according to claim 1, wherein the titanium alloy rod has properties under JIS of: a) tensile strength is greater than or equal to 1,150 MPa, b) fatigue strength is greater than 900 MPa, c) elastic modulus is less than 110 GPa, d) 0.2% proof stress is greater than 1,000 MPa, and e) percentage elongation after fracture is greater than or equal to 15%.

* * * * *